United States Patent
Cordery et al.

(10) Patent No.: US 6,852,539 B2
(45) Date of Patent: Feb. 8, 2005

(54) METHOD AND SYSTEM FOR DETECTION OF CONTAMINANTS IN MAIL

(75) Inventors: Robert A. Cordery, Danbury, CT (US); Pushpavadan S. Nagarsheth, Danbury, CT (US); Joseph E. Wall, Fairfield, CT (US)

(73) Assignee: Pitney Bowes Inc., Stamford, CT (US)

( * ) Notice: Subject to any disclaimer, the term of this patent is extended or adjusted under 35 U.S.C. 154(b) by 289 days.

(21) Appl. No.: 10/034,913

(22) Filed: Dec. 18, 2001

(65) Prior Publication Data

US 2003/0114957 A1 Jun. 19, 2003

(51) Int. Cl.⁷ ............................................... G01N 31/00
(52) U.S. Cl. ......................... 436/1; 436/174; 422/83; 422/119; 73/12.04; 73/28.01; 73/31.03; 73/864.33; 220/231
(58) Field of Search ....................... 422/58, 61, 83, 422/117, 119; 436/1, 2, 43, 174, 175, 86; 73/12.04, 28.01, 31.01–31.03, 864.33; 220/231

(56) References Cited

U.S. PATENT DOCUMENTS

| | | | | |
|---|---|---|---|---|
| 4,580,440 A | * | 4/1986 | Reid et al. .................. | 73/31.07 |
| 5,942,699 A | * | 8/1999 | Ornath et al. ............ | 73/863.21 |
| 6,441,743 B1 | * | 8/2002 | Berger ........................ | 340/603 |
| 6,573,836 B1 | * | 6/2003 | Gitis et al. .................. | 340/603 |
| 2003/0119175 A1 | * | 6/2003 | Stradley et al. .......... | 435/287.1 |
| 2003/0136179 A1 | * | 7/2003 | Felice et al. ............... | 73/31.03 |
| 2003/0136203 A1 | * | 7/2003 | Yoon ........................ | 73/864.33 |
| 2004/0020264 A1 | * | 2/2004 | Megerle .................... | 73/19.01 |
| 2004/0045342 A1 | * | 3/2004 | Jones et al. ..................... | 73/37 |

* cited by examiner

*Primary Examiner*—Lyle A. Alexander
(74) *Attorney, Agent, or Firm*—Brian A. Lemm; Angelo N. Chaclas

(57) ABSTRACT

A contaminant detection system for mail is provided. A tray of mailpieces is transported along a transport path into a chamber that has a negative pressure maintained by a vacuum system. The tray of mail enters the chamber and is quickly decelerated, such as, for example, by hitting a stop. The quick deceleration compresses the mailpieces in the tray, thereby ejecting air, dust and other particles from the mailpieces into the surrounding environment inside of the chamber. The vacuum system draws the ejected air, dust and other particles into a sampling system that monitors for the presence of a possible biohazard. If any type of contaminant is found in the ejected air, dust and other particles, the tray can be held for further investigation of the mailpieces. If no contaminants are detected, the tray is accepted and the mailpieces are further processed.

10 Claims, 2 Drawing Sheets

METHOD AND SYSTEM FOR DETECTION OF CONTAMINANTS IN MAIL

FIELD OF THE INVENTION

The invention disclosed herein relates generally to the processing of mail, and more particularly to a method and system to detect possible contaminants contained within or on a mailpiece.

BACKGROUND OF THE INVENTION

The United States currently has the world's largest postal system, which handles billions of pieces of mail each year. The servicing of mail delivery involves three general steps: collection, sorting, and delivery. Collection takes place through a series of local post office facilities and Bulk Mail Entry Units (BMEU) spread throughout the United States. The mail is then sent from local post offices or BMEUs to central facilities known as sectional centers. At the sectional centers, high speed automated equipment sorts the large volumes of mail based on the destination post office or zip code for delivery.

Recently, the postal system has been used as a weapon of terror and fear by the inclusion of harmful chemical or biological contaminants, such as, for example, the spore-forming bacterium *Bacillus anthracis* (anthrax), within or on a mailpiece. Such contaminants can be carried in several forms, including for example, a powder form. The harmful effects of only a few contaminated mailpieces can be far reaching, as cross-contamination of other mailpieces can easily occur when the mailpieces come in contact with each other or are passed through the same machines during sorting.

Ideally, it would be desirous for the postal authority to examine and/or test each piece of mail individually for any possible contamination before it enters the mail system, thereby isolating any contaminated mailpieces and preventing any cross-contamination. With the large volume of mail processed daily, however, such an approach is not feasible due to the time and cost that such an undertaking would entail.

Thus, there exists a need for a method and system that allows large volumes of mailpieces to be tested for any possible biohazard contaminants in a relatively short time and in a manner similar to existing to mail handling.

SUMMARY OF THE INVENTION

The present invention alleviates the problems associated with the prior art and provides a method and system that allows large volumes of mailpieces to be tested for any possible biohazard contaminants in a relatively short time and in a manner similar to existing to mail handling.

In accordance with the present invention, a contaminant detection system for trays of mail is provided. A tray of mailpieces is transported along a transport path into a chamber that has a negative pressure maintained by a vacuum system. The tray of mail enters the chamber and is quickly decelerated, such as, for example, by hitting a stop. The quick deceleration compresses the mailpieces in the tray, thereby ejecting air, dust and other particles from the mailpieces into the surrounding environment inside of the chamber. The vacuum system draws the ejected air, dust and other particles into a sampling system that monitors for the presence of a possible biohazard. If any type of contaminant is found in the ejected air, dust and other particles, the tray can be held for further investigation of the mailpieces. If no contaminants are detected, the tray is accepted and the mailpieces are further processed by normal processing means.

DESCRIPTION OF THE DRAWINGS

The above and other objects and advantages of the present invention will be apparent upon consideration of the following detailed description, taken in conjunction with accompanying drawings, in which like reference characters refer to like parts throughout, and in which.

DETAILED DESCRIPTION OF THE PRESENT INVENTION

Figure 1:
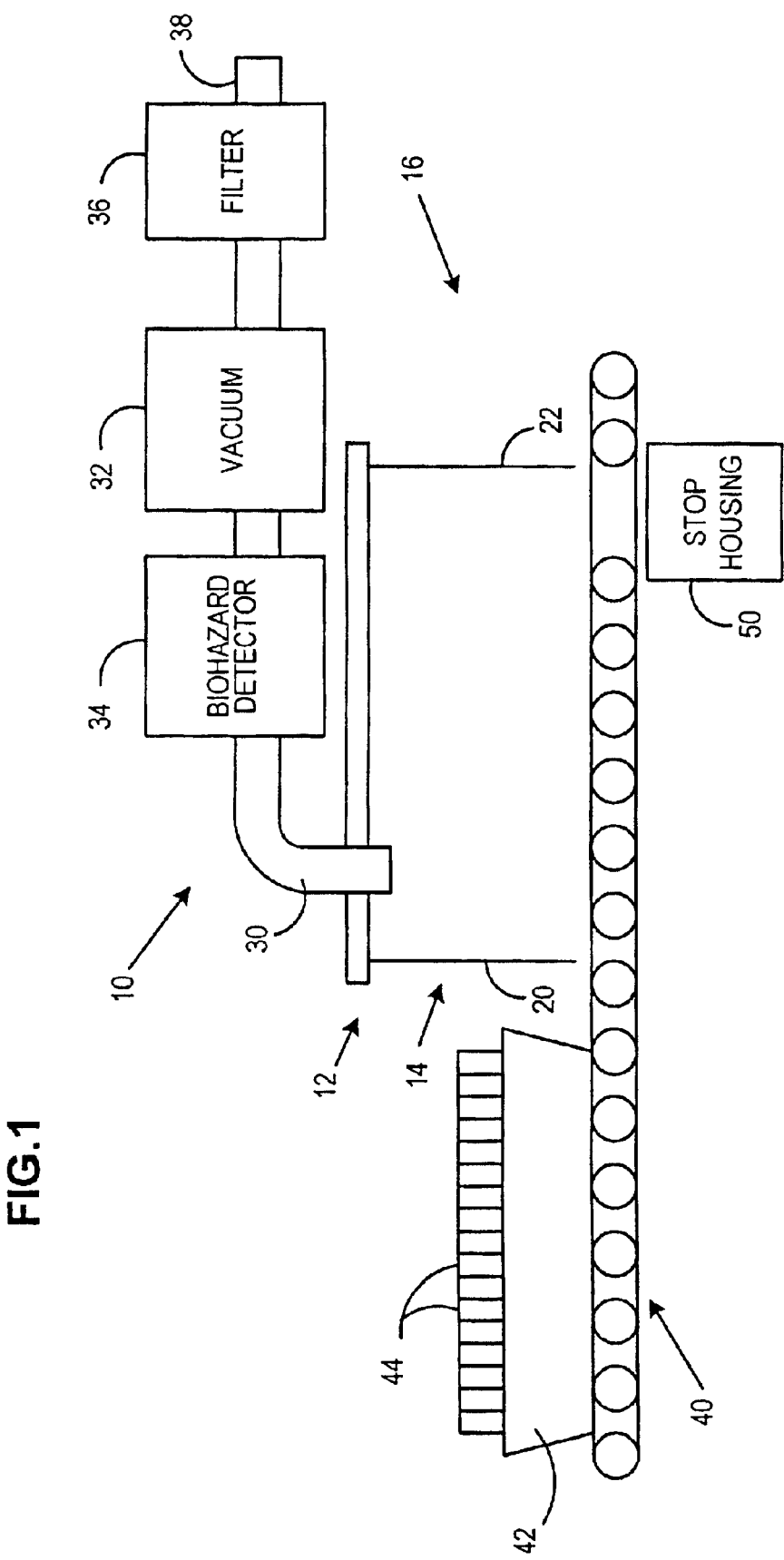
FIG. 1 illustrates in block diagram form a contaminant detection system according to the present invention before a mail tray has entered.

In describing the present invention, reference is made to the drawings, wherein there is seen in FIG. 1 a system 10 for contaminant detection according to the present invention. System 10 includes a test chamber 12 having an inlet side 14 and an outlet side 16. Inlet side 14 is provided with an inlet curtain 20, and outlet side 16 is provided with an outlet curtain 22. The inlet curtain 20 and outlet curtain 22 are utilized to reduce the amount of exchange of air and dust particles between the inside of chamber 12 and the outside environment surrounding the chamber 12. A stop housing 50, further described below, is provided near the outlet side 16 of chamber 12.

A negative pressure is maintained inside of chamber 12 by a vacuum system 32 via vacuum intake tube 30. Air and dust particles from the inside of chamber 12 are pulled into intake tube 30 and passed through a biohazard detector 34 by vacuum system 32. The exhaust 38 from vacuum system 32 is preferably passed through a biohazard blocking filter 36, such as, for example, a High Efficiency Particle Arresting (HEPA) filter, that removes the majority of harmful particles, including dust and spores, from the air taken from within chamber 12. Optionally, filter 36 can also incorporate a biocide to kill any type of microorganisms that are collected by vacuum 32.

A transport 40 is utilized to transport a tray 42 to chamber 12. Tray 42 includes a plurality of mailpieces 44. Transport 40 could be, for example, a belt/roller combination as illustrated. Tray 42 is similar to existing trays currently utilized by the postal authority for mail handling, thereby allowing the system 10 to be utilized within existing mail handling procedures.

Figure 2:
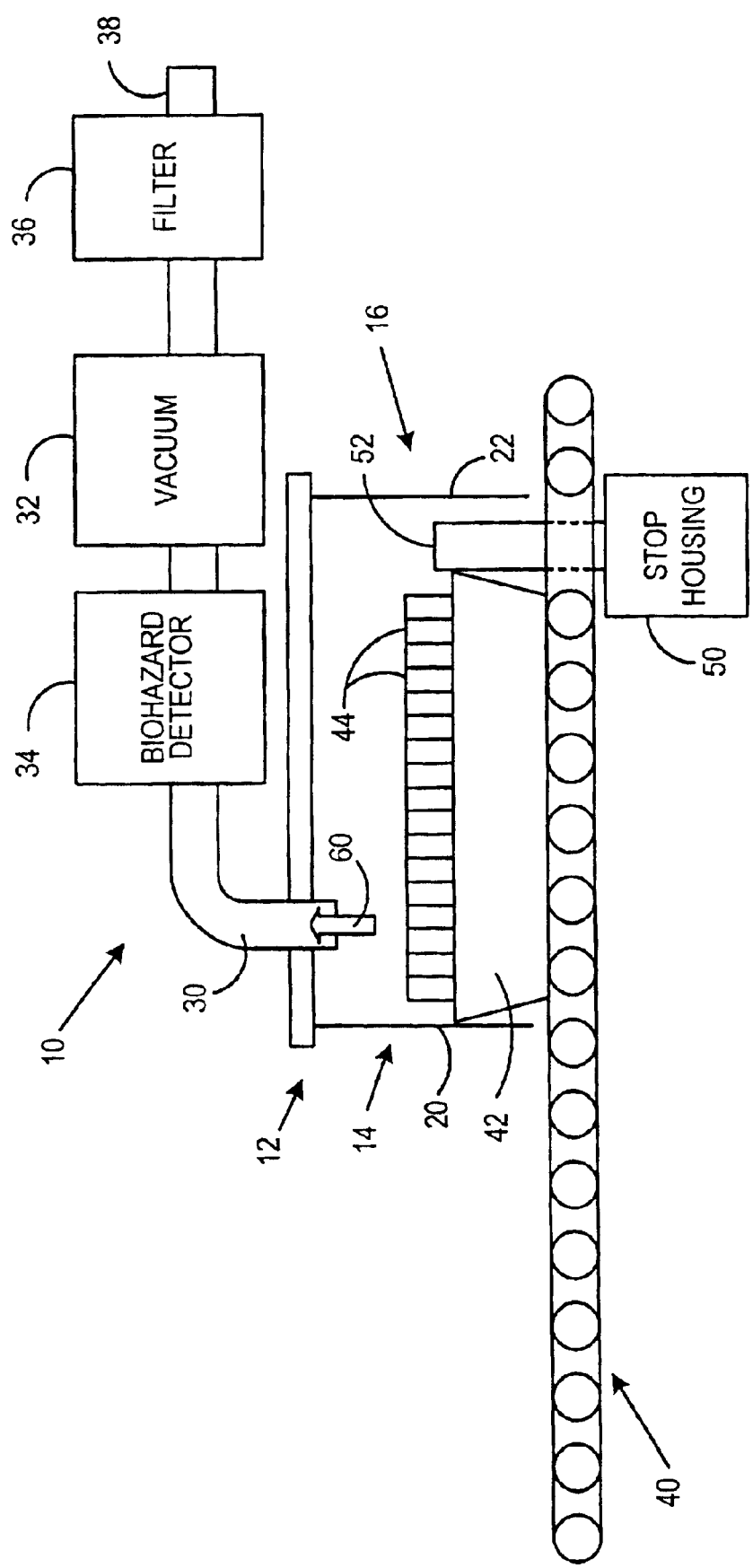
FIG. 2 illustrates in block diagram form the contaminant detection system according to the present invention after a mail tray has entered.

The operation of system 10 will now be described with respect to FIG. 2. The tray 42 of mailpieces 44 approaches the inlet side 14 of chamber 12 and the inlet curtain 20 is moved to allow tray 42 to enter the chamber 12. Inlet curtain 20 can be opened either automatically upon detection of tray 42 approaching, or alternatively can be opened by the force exerted upon it from tray 42. The inlet curtain 20 returns to its original position, thereby partially sealing the inlet side 14 of chamber 12, once the tray 42 has entered the chamber 12.

When the tray 42 is inside of chamber 12, it is quickly decelerated, thereby causing the mailpieces 44 in the tray 42 to suddenly compress. Such deceleration can be caused, for example, by tray 42 hitting a stop member 52 that is projected from the stop housing 50 into the path of tray 42 on transport 40. Preferably, stop member 52 is positioned along transport 40 inside of the chamber 12. Stop member 52 could, however, be positioned outside of the chamber 12 just past the outlet curtain 22. The sudden compression of the mailpieces in tray 42 from the quick deceleration of tray 42 causes any air, dust and any other particles in and on the mailpieces 44 to aerosolize, i.e., to become airborne within the chamber 12. For example, if one or more of the mailpieces 44 contains a contaminant carried in the form of a powder, the sudden compression of the mailpieces 44 will cause some of the powder to be ejected from the mailpiece 44. To ensure sufficient compression of the mailpieces 44 to eject air, dust and other particles, the tray 42 is preferably accelerated by transport 40 before entering the chamber 12, or alternatively, upon entering the chamber 12. The vacuum 32 draws the ejected air, dust and other particles from the inside of chamber 12 in the direction of arrow 60 through the intake tube 30 and into biohazard detector 34.

Detector 34 analyzes the ejected air, dust and other particles to detect any type of biohazards. Detector 34 can, for example, analyze the ejected air, dust and other particles for the presence of excessive aerosol, i.e., floating particles, indicating possible contaminants in an aerosolized form. Additionally, detector 34 could analyze the ejected air, dust and other particles for particular contaminants. For example, detector 34 could utilize optical or electrostatic characteristics to determine if a particular contaminant is present. It should be understood that the above are examples only, and any type of detection system for contaminants can be utilized with the present invention.

As noted above, the exhaust 38 from vacuum system 32 is preferably passed through a biohazard blocking filter 36, such as, for example, a High Efficiency Particle Arresting (HEPA) filter, that removes the majority of harmful particles, including dust and spores, from the air taken from within chamber 12. Optionally, filter 36 can also incorporate a biocide to kill any type of microorganisms or other contaminants that are collected by vacuum 32.

If detector 34 determines that no excessive aerosol is detected, or the particular biohazards being tested for are not detected in the ejected air, dust and particles, then the tray 42 will be accepted and the stop member 52 will retract into the stop housing 50, thereby allowing the tray 42 to pass through the chamber 12 and continue on a path to normal mail processing. If detector 34 determines that an excessive amount of aerosol is present, or that one or more of the particular biohazards being tested for are detected in the ejected air, dust and particles, then the detector 34 will provide a signal that the tray 42 may contain a possible biohazard. Stop member 52 will retract into the stop housing 50, thereby allowing the tray 42 to pass through the chamber 12, where it can be diverted from the normal mail processing path to a reject path for further investigation of the mailpieces 44 held in tray 42.

By utilizing the system 10 according to the present invention, an entire tray 42 of mailpieces 44 can be tested simultaneously, thereby significantly reducing the amount of time required for testing as compared to individually testing each mailpiece 44. Additionally, by utilizing the system 10 according to the present invention upon mail acceptance and before sending the mailpieces through sorting equipment of a normal mail processing path, cross-contamination of the sorting equipment, and any subsequent mailpieces that pass through the sorting equipment, can be prevented.

It should be understood that although the present invention was described with respect to mail processing by a post office, the present invention is not so limited and can be utilized in any application in which a large amount of mail is received. For example, the detection system could also be utilized by a business or company that receives large amounts of mail upon receipt of the mail. By utilizing the present invention at mail acceptance, prior to sorting the mail in the mailroom for internal delivery, contamination of the company's sorting machines, as well as cross-contamination of any other mailpieces, can be prevented.

While a preferred embodiment of the invention has been described and illustrated above, it should be understood that this is exemplary of the invention and is not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. A method for testing a tray of mail for a contaminant comprising the steps of:

moving the tray of mail along a transport path;

projecting a stop member into the transport path;

moving the tray into the stop member in the transport path, thereby stopping movement of the tray of mail along the transport path and compressing the mail in the tray, the compression causing matter contained within and on the mail in the tray to become airborne into a surrounding environment of the tray of mail;

collecting a sample from the surrounding environment of the tray of mail;

analyzing the sample from the surrounding environment to determine if a contaminant may be present;

retracting the stop member from the transport path;

sending the tray of mail to a normal processing path if it is determined a contaminant is not present; and diverting the tray of mail from the normal processing path if it is determined a contaminant is present.

2. The method according to claim 1, wherein before the tray is moved into the stop member the method further comprises:

accelerating movement of the tray along the transport path.

3. The method according to claim 1 wherein the step of collecting further comprises:

using a vacuum system to collect the sample.

4. The method according to claim 1 wherein the step of analyzing further comprises:

analyzing the sample for an aerosol.

5. The method according to claim 1, wherein the step of analyzing further comprises:

analyzing the sample for a specific contaminant.

6. A system for testing a tray of mailpieces for a contaminant comprising:

a test chamber;

a transport path to transport the tray of mailpieces through the test chamber;

a stop member located along the transport path, the stop member having a first position in which it is projected into the transport and a second position in which it is retracted from the transport path;

a detection system to collect and analyze a sample taken from within the test chamber;

a first processing path located downstream of the test chamber; and a second processing path located downstream of the test chamber, wherein movement of the tray of mailpieces is stopped inside the test chamber by the tray of mailpieces making contact with the stop member when the stop member is in the first position, the stoppage of the movement causing the mailpieces to compress thereby causing matter contained within and on the mailpieces in the tray to become airborne inside the test chamber, the detection system collects a sample from inside the test chamber and analyzes the sample to determine if a contaminant may be present in the matter contained within and on the mailpieces, the stop member moves to the second position and the tray of mailpieces is sent to the first processing path if it is determined a contaminant is not present and to the second processing path if it is determined a contaminant is present.

7. The system according to claim 6, wherein the detection system further comprises:

a detection unit to detect contaminants; and a vacuum to draw the sample from inside the test chamber to the detection unit.

8. The system according to claim 8, wherein the detection unit analyzes the sample for an aerosol.

9. The system according to claim 7, wherein the detection unit analyzes the sample for a particular contaminant.

10. The system according to claim 6, wherein the transport path accelerates the tray of mailpieces before making contact with the stop member.

* * * * *